(12) United States Patent
Monro

(10) Patent No.: US 6,506,346 B1
(45) Date of Patent: Jan. 14, 2003

(54) DIAGNOSTIC TEST CONTAINER AND METHOD OF SAMPLING

(75) Inventor: Philip Monro, Dorset (GB)

(73) Assignee: Hampshire Advisory and Technical Services Limited (GB)

( * ) Notice: Subject to any disclaimer, the term of this patent is extended or adjusted under 35 U.S.C. 154(b) by 0 days.

(21) Appl. No.: 09/248,602

(22) Filed: Feb. 11, 1999

Related U.S. Application Data

(63) Continuation of application No. PCT/GB96/01953, filed on Aug. 12, 1996.

(51) Int. Cl.[7] .............................................. G01N 33/48
(52) U.S. Cl. ................... 422/102; 422/103; 435/297.1; 436/169
(58) Field of Search ............................. 422/58, 61, 97, 422/100–103; 436/164, 169; 435/297.2, 297.1

(56) References Cited

U.S. PATENT DOCUMENTS

| | | | |
|---|---|---|---|
| 3,657,073 A | 4/1972 | Burton et al. | ................ 195/127 |
| 3,865,548 A | 2/1975 | Padawer | |
| 3,893,891 A | 7/1975 | Tannenbaum et al. | ...... 195/127 |
| 4,131,549 A | 12/1978 | Ferrara | |
| 4,865,813 A | 9/1989 | Leon | ........................... 422/101 |
| 5,116,759 A | 5/1992 | Klainer et al. | ............... 435/288 |
| 5,215,102 A | 6/1993 | Guirguis | |
| 5,490,971 A | 2/1996 | Gifford et al. | ................. 422/58 |
| 5,525,475 A | 6/1996 | Ladouceur | ................... 435/7.9 |
| 5,882,318 A | * 3/1999 | Boyde | ......................... 600/595 |

FOREIGN PATENT DOCUMENTS

WO    WO 91/14466    10/1991

* cited by examiner

*Primary Examiner*—Lyle A. Alexander
(74) *Attorney, Agent, or Firm*—Wolf, Greenfield & Sacks, P.C.

(57) ABSTRACT

A container has a single primary chamber linked to a single secondary chamber via a common wall in which has been fused a semi-permeable membrane. A lid for the primary chamber enables sealing of a sample (not shown) inserted into the primary chamber, sealingly enclosing any dangerous fraction of the sample, which fraction and the lid closed any infectious material hermetically sealed in as this cannot cross the semi-permeable membrane, due to the latter being provided with a cut-off matched to the molecular size of the type of sample with which the container is to be used. However, material of a lower molecular weight than the dangerous fraction can move across the membrane in either directions by dialysis or osmosis.

42 Claims, 12 Drawing Sheets

DIAGNOSTIC TEST CONTAINER AND METHOD OF SAMPLING

This application is a continuation of application No. PCT/GB96/01953, filed Aug. 12, 1996, entitled "Diagnostic Test Container" and now pending.

FIELD OF THE INVENTION

This invention relates to a diagnostic test container for the analysis of potentially infectious or toxic material.

BACKGROUND

The increased incidence of highly infectious diseases and chemical contamination poses two independent problems for the pathology services:

1. To safely detect these highly infectious diseases;
2. To safely carry out other tests on samples that may concurrently be infected or contaminated or are thought to be infected or contaminated.

The object of the present invention is to reduce the risks associated with these tests.

Existing Technology

It is known to use membranes to produce filtrates for chemical analysis. It is also known to retain infectious material in a test container by means of a bacteria-retaining membrane, as described for example in U.S. patent specification No. 4,421,849, which states that "the filter should have pores from 0.22 to 0.45 (microns) to ensure microorganism impermeability".

However it should be noted that such a membrane will not retain viruses; and that carrying out tests on material containing viruses without taking additional steps to retain them potentially exposes the tester to the viruses.

In our patent application No. PCT/GB91/00446, published under No. WO 91/14466, we described:

1. A method of testing a potentially infectious substance, from the group of blood- tissue- or other biological-substances, the method consisting in the steps of:
   enclosing and sealing the substance to be tested in a closed container of which at least a part is formed of semi-permeable membrane, the semi-permeable membrane having a molecular weight cut-off such that viruses and other potentially infectious organisms are retained within the container by virtue of having a molecular weight higher than the molecular weight cut-off of the membrane, and
   contacting the semi-permeable membrane with a test reagent having a molecular weight lower than the molecular weight cut-off of the membrane and allowing the test reagent to pass through the membrane and react with the substance.
2. A method of testing a potentially infectious substance, from the group of blood- tissue- or other biological-substances, the method consisting in the steps of:
   enclosing and sealing the substance to be tested in a closed container of which at least a part is formed of semi-permeable membrane, the semi-permeable membrane having a molecular weight cut-off such that viruses and other potentially infectious organisms are retained within the container by virtue of having a molecular weight higher than the molecular weight cut-off of the membrane, and
   contacting the semi-permeable membrane with a test reagent whereby substances on which tests are to be performed and which are of lower molecular weight than the molecular weight cut-off of the membrane can pass out of the container to react with the test reagents.

The difference between these two methods is that in the first the reagent passes into the closed container and reacts there; and in the second the testable substance passes out of the closed container for reaction. The mechanisms for movement of the reagent and testable substance are predominantly osmotically driven ultra-filtration and dialysis. The membrane is viral tight and provides a truly aseptic barrier.

The Invention

An object of the present invention is to enable these tests to be carried out in a self-contained manner.

According to the present invention we provide a container for testing a sample liable to include a potentially infectious, toxic or dangerous material, the container comprising:
   one or more primary chambers for retaining potentially infectious, toxic or dangerous substances,
   means for sealing a sample into the primary chamber(s),
   one or more secondary chambers linked to the primary chamber(s) via at least one common wall(s) and a
   a semi-permeable membrane incorporated in the common wall(s),
   the semi-permeable membrane having a molecular weight/effective molecular diameter or configuration cut-off such that potentially infectious, toxic or dangerous material placed and sealed in the primary chamber(s) is retained there by virtue of having a molecular weight higher than the molecular weight cut-off of the membrane.

With such a container potentially infectious, toxic or dangerous material of higher molecular weight or effective molecular diameter than the membrane's cut-off remain sealed within the primary chamber(s). Hereinafter, the term "molecular size" in the context of the membrane's cut-off will mean that the molecular weight or effective molecular diameter or configuration (i.e. effective minimum cross-sectional shape inhibiting passage through the membrane) is such that the substance concerned will not pass through the membrane because it is too large for the pore size of the membrane.

Many types of test or assay can be carried out on material in or released from the sample in the primary chamber(s) but it is envisaged that most uses of the containers of the invention will be either of the two following:

a) Those where test reagent(s) in the secondary chamber(s) having a lower molecular size than the cut-off of the membrane pass through the membrane(s) and react with material retained within the primary chamber(s). For instance, these include assays such as the direct detection of viral bodies or the determination of blood groups. In containers for these the membrane is selected to allow through relatively large proteins but completely block the movement of viral particles;

b) Those where a lower molecular size fraction from the primary chamber(s) passes into the secondary chambers for reaction with reagents therein.

The simplest embodiment of the invention will be a container having two chambers separated from each other by a single semi-permeable membrane, the material to be assayed being placed and sealed in the primary chamber and reagents being placed in the secondary chamber As used hereinafter, the term the "sample" means the potentially infectious, toxic or dangerous material that is placed and then sealed within the primary chamber(s). It can be any biological material which is dead or alive, intact or in parts. It could come from any animal or plant species or microorganism including, but not restricted to, bacteria, viruses, fungal and other botanical material as well as prions. Most commonly, but not exclusively, these samples will blood and related fluids, urine samples, faecal samples (solid or liquid), cells, tissues or organs or exudates. The material of biological origin may constitute all or part of the specimen including live specimens. The dangerous component of this material will vary in effective molecular size, and the semi-permeable membrane will be chosen to have an appropriate cut-off to ensure that the dangerous component cannot pass through the membrane and will be retained in the primary chamber(s).

Choice of the semi-permeable membrane is critical not only for retaining the potentially infectious, toxic or dangerous fraction (hereinafter called the "dangerous fraction") of the sample within the primary chamber(s), but also for allowing passage of relatively safe fractions from the sample and/or reagents to it. Thus the membrane's cut-off must not only be low enough to prevent passage of the dangerous fraction but also be high enough to facilitate maximum movement of these fractions and reagents.

Membranes are now readily available with a wide range of molecular porosities and varying physical properties including physical strength, chemical structure and physical form and it is possible to select a membrane with a porosity that ranges from a few hundred to many million Daltons and beyond that to any macro-porosity. Materials that are used for membranes include cellulose film, PTFE, polyurethane acrylic copolymers, cellulose acetate, polyalginate, polysulfone, polyvinyl alcohols, polyvinylidene fluoride, polyacryl nitriles and derivatives and mixtures of these.

The following table gives the molecular size range (in microns) of various ranges of substances, and examples of suitable membranes for preventing their passage whilst allowing passage of smaller molecules:

TABLE 1

| | Typical Molecular size | Membrane Material | Membrane Reference |
|---|---|---|---|
| Bacteria | 0.5–60 | Cellulose acetate | S&S 0E66 |
| Viruses | 0.01–0.7 | Cellulose nitrate | S&S PH75 |
| Proteins | 0.004–0.02 | Cellulose nitrate | S&S PH70 |
| Endotoxins | 0.003–0.02 | Cellulose nitrate | S&S PH70 |
| Amino Acids | 0.0004–0.006 | Cellulose ester | Or 131084 |
| Salts | 0.0001–0.0005 | Zeolites | Smart |

Note:
The membrane reference includes the following manufacture abbreviations:
S&S:- Scheichler & Schuell Inc., Dassel, Germany
Orme:- Orme Technology, Manchester, England
Smart:- Smart Chemical Company, London, England.

It will be appreciated that in certain embodiments material should be contained that is toxic or dangerous while not actually infectious. An example of this type of material are many lectins whose total containment would be advantageous on safety grounds. For example, if for instance, a container of the invention was to be made in which it was essential to retain toxins from Ricinus communis (form RCA60) a membrane would be used with a cut-off of approximately 50,000 Daltons.

It will be realised that for those embodiments where the effective pore size of the membrane can be increased this will increase the rate of movement of solutes and solvents and where appropriate the time to reach equilibrium will be reduced.

In one alternative, the semi-permeable membrane occupies the upper part of the common wall; in another, the semi-permeable membrane occupies the lower part of the common wall.

Preferably, the the primary chamber(s) with a dangerous fraction of the sample retained therein is/are separable from the secondary chamber(s).

In certain embodiments, the primary chamber consists substantially of semi-permeable membrane, whereby it and its contents can be removed from the secondary chamber.

Preferably, at least one of the chambers is of clear material to allow the contents to be seen and preferably facilitate the direct assay of their contents in any part of the electromagnetic spectrum. Normally, the container will have an optically clear wall portion of one of the chambers to facilitate the direct examination of their contents using a microscope, preferably an inverted microscope via the optically clear wall portion.

A single primary chamber may be connected to multiple secondary chambers, whereby more than one separate assay can be determined on the contents of the same primary chamber.

Alternatively or indeed additionally, multiple primary chambers may be connected to a single secondary chamber so that multiple identical or dissimilar assays can be carried out at the same time but using a common pool of reagents.

Conveniently one or more of the chambers includes means for adding or removing a specific volume or mass of reagent or biological material.

Means may be provided for enhancing the speed and/or mass of movement of contents through the semi-permeable membrane.

The semi-permeable membrane may be coated or treated to enhance or inhibit the movement of specific solutes or solvents. Further it may be reinforced and/or supported on either side, using by way of example only a nylon mesh.

Some or all of the chambers may be pre-loaded with dried or liquid reagents prior to its use. Alternatively or additionally some or all of the chambers are pre-loaded with living or dead reference microorganisms or standard masses of reference reagents. Again some or all of the chambers may contain substances which act as an osmotic driver and/or dialysing substance to enhance the movement of solvent and/or solute across the semi-permeable membrane in any appropriate direction. Further some or all chambers can contain substances which are capable of rehydration and/or are hygroscopic and so enhance, the movement of solvent and/or solute across the semi-permeable membrane in any appropriate direction, the substances preferably being in the secondary chamber(s) to concentrate the material in the primary chamber.

In some embodiments, the secondary chamber(s) is/are open to allow for the removal and/or rinsing and/or dilution of all or part of its contents. Alternatively, the secondary chamber(s) may be provided with lid(s).

Conveniently one or more chamber contains chemical or physical binding agents that bind specific substances to reduce the movement of all or specific components that would normally move across the semi-permeable membrane and/or reduce their participation in subsequent chemical reactions.

In one embodiment, two or more chambers are placed in sequence each separated by a semi-permeable membrane which may have similar or dissimilar properties and structure.

Preferably one or more of the chambers contains a device for indicating that a specific volume of liquid is present in any particular chamber to enable quantitative or at least semi-quantitative assays to be carried out.

Again, one or more of the chambers preferably contains a specific substance that provides visible, chemical or physical evidence that there had been a breach of the integrity of the primary chamber(s).

The container may include multiple layer membranes.

In one embodiment, dry solutes, solutes or solutions are sealed in a sub-compartment of one or more of the chambers from which it is separated by a burstable septum which can be broken at an appropriate time without affecting the total integrity the whole chamber.

In another embodiment, a vacuum seal is included for at least the primary chamber(s) and there is also provided a seal adapted for introduction of a sample via a needle and re-sealing after withdrawal of the needle, whereby the container can be evacuated for the drawing of the sample into the container.

According to the invention there is also provided a method of testing a sample including a dangerous fraction the sample being contained in one or more of the primary chamber(s) of a container of the invention, the method including the step of allowing material initially present in the primary chamber(s) and having a lower molecular size than the cut-off of the membrane to pass through the membrane and react with material within the secondary chamber(s) whilst the dangerous fraction is retained within the primary chamber(s).

In another method in accordance.with the invention of testing a sample including a dangerous fraction the sample being contained in one or more of the primary chamber(s) of a container of the invention, the method including the step of allowing material initially present in the secondary chamber(s) and having a smaller molecular size than the cut-off of the membrane to pass through the membrane and react with material within the primary chamber(s) whilst the dangerous fraction is retained within the primary chamber (s).

The methods may include the preliminary step of culturing living organisms in the primary chamber(s) prior to their identification. Subsequently to testing a disinfecting substance, and/or toxic neutralising agent is added to the secondary chamber(s) and allowed to permeate through the semi-permeable membrane to the primary chamber(s).

A particular feature of the method, where the secondary chamber(s) contain water absorbing substances, is that these substances are allowed to extract substantially all water from the sample.

The membrane will usually be of flexible sheet material. However it is envisaged that it may be rigid to strengthen it, particularly where a pressure differential will be applied across it in use. Alternatively, it may be reinforced by fusing or otherwise connecting it to a porous reinforcing member or mesh which can be on either side (or both sides) of any membrane.

The membrane may be coated, impregnated or otherwise treated to enhance or reduce the movement of specific solutes or solvents. Typically, coating with a hydrophobic substance reduces movement of water through the membrane. Fluting or surface treatment as by rolling in micro-indentations can increase the rate, speed and mass at which solute and solvent move across the membrane.

The membrane may be a compound membrane comprised of multiple layers of different membrane material, with one at least having a pore size to prevent the dangerous fraction passing. The layers may be fused together or separate. Separating them can produce a sequence of chambers each separated by a semi-permeable membrane which may have similar or dissimilar properties and structure. For example, a 1 micron. membrane within the primary chamber could be used to fractionate red blood cells within a sealed primary chamber by adding the sample to only one of these sub-compartments within the primary chamber.

It is anticipated that multi-layered fused membranes will reduce the risk of inter-chamber leakage, since it is unlikely that a defect in one layer will be superimposed on a defect in another layer.

Further, it is anticipated that the primary sealed chamber (s) could be made entirely of semi-permeable membrane and inserted in a re-usable secondary chamber.

In another embodiment, for fractionating substances in the sample, a series of interconnected secondary chambers each being divided from the next by a membrane with a different property, the membrane in the common wall between the primary chamber and the first secondary chamber being such as to retain the dangerous fraction.

Normally the membrane will extend over the maximum practical extent of the common wall, with the container being designed to be upstanding, typically 10 cm high. Nevertheless, the membrane may for instance be restricted to the upper part of the common wall to reduce the risk of stress or physical damage due to the forces generated during centrifugation or other separation procedures.

Alternatively, it could be placed to specifically enhance any physical or chemical process that can be used to move material between compartments Substances may be incorporated in the container to indicate defects in the integrity of the primary chamber. For example, a trace of blue dextran (molecular weight c500, 000, i.e. smaller than a virus) may be provided in the primary chamber. If its blue colour is seen in the secondary chamber, this will indicate leakage through the membrane. Alternatively, two high molecular weight reagents may be provided in the respective chambers on opposite sides of the membrane. Their reaction in either chamber will indicate breach of the membrane. The reagents and any resulting products must of course be inert with respect to the use of the container. As the size of the defect in the membrane could be relatively small an ideal chemical reaction would be one where there was an amplification stage.

The chambers of the container may be of predetermined volume or contain volume indicators to enable quantitative or at least semi-quantitative assays to be carried out. The secondary chambers may be designed to specifically accommodate sampling devices intended for semi-automatic or fully automatic assay systems.

Neutral chemical or physical binding agents may be incorporated in the chambers to reduce the movement of specific solvents or solutes between the primary and secondary chambers using substances placed in the chambers or as coatings on or contained within the membrane.

The container may incorporate multiple secondary chambers, whereby by use of appropriate distinct reagents different assays can be performed on the same sample. A series of containers could be made each provided with specific reagents for different test procedures. Ideally these should be designed to minimize or avoid cross-contamination between the multiple compartments.

Similarly, another container can incorporate multiple primary chambers connected to a single secondary chamber so that multiple identical or dissimilar assays can be carried out at the same time but using a common pool of reagents. Again both multiple primary and secondary chambers can be provided.

Preferably, the chambers of the container are of optically clear material, to enable their contents to be seen or analysed through the walls of the chamber. Optical analysis can be enhanced by:
1. Providing a defined solvent path of say one centimetre to enable contents to be analysed directly with a spectrophotometer.
2. Providing an adaption for examination by microscope.

Neutral chemical or physical agents may be incorporated in either chamber to enhance the movement of specific solvents or solutes between the primary and secondary chambers. These, by way of example only, could include high molecular weight dextrans, ionic dextrans (or similar disassociating solutes), hydroscopic and delequescent substances or material that incorporates a large mass of water into its molecular structure. The latter include high molecular weight polyelectrolytes e.g. Salsorb (TM) made by Allied Colloids Ltd. For maximum effect the substances used would have a molecular weight slightly larger than the pore size of the membrane being used. By placing a relatively large fraction of such material in the secondary chamber all or a significant fraction of any solute or solvent present in the primary chamber can be extracted to the secondary chamber while at the same time ensuring that all infectious or toxic material remain in the primary chamber.

It will be appreciated that in such an embodiment the infectious material is concentrated and so would be available for assay or other uses.

Where visual observations are being made such material should be transparent with respect to the wavelength being used.

In other embodiments those substances that enhance the movement of solvents or solutes across the membrane could have assay reagents incorporated into their structure or bound to their surface. This could, by way of example only, enable a qualitative assay to be completed as soon as the dissolved solute came into contact with the rehydrating substance. If, for instance, iodine were bound to the assay reagents in a secondary chamber(s), then if a solution containing polysaccharides were to come into contact with this substance it would turn black.

Embodiments can be envisaged to facilitate or enhance those processes and forces that enhance the movement of material across the membrane. These would include by way of example only centrifugation, ultrasound, vibration, a vacuum, shaking, stirring, heating and agitation and the use of electrophoresis and reverse iontophoresis. For example vanes could be placed on the external surface of one or more chambers to fit into proprietary agitation systems. Similarly embodiments could be specifically designed to facilitate centrifugation.

For specific assays containers can be constructed in which a number of chambers are pre-loaded with reagents (in liquid or dried form) prior to use. This pre-loaded material could be placed in any number of sub-compartments which could be separated from a maim chamber(s) via by way of example only, a breakable septum. By preloading appropriate chambers with standard masses of reference material, the containers can be used for calibration or identification purposes. In this case it may be advisable for the secondary chamber(s) to be provide with a removable lid.

It is common practice now to use a vacuum to draw blood into a primary blood collection tube. The Vacuette (TM) by Greiner Labortechnik, Kremsmunster, Austria is typical of this type of product. Similarly, it is preferred to adapt the container of the invention, at least for use in analysing blood samples, to enable samples to be collected in this way. By way of example only, such an embodiment could have a rigid semi-permeable membrane between the primary and secondary chambers, so that when the primary chamber is evacuated or filled the membrane is not damaged.

The sample can be sealed in the primary chamber by any of a wide range of sealing techniques, as used for instance to seal samples into existing sample collection tubes. By way of example only this includes a screw cap, which current laboratory practice has shown to be safe in completely sealing in potentially infected material. Alternatively push fit seals are suitable. In addition the invention can utilise septum seal, such as a rubber cap, through which a sample can be added to the primary chamber but which will remain sealed once the sample has been added.

Normally, the multiple chambers will be permanently fixed together. However, for certain applications, it may be advantageous to separate off specific chambers and their contents. In these embodiments there will be retention of the total integrity of the primary chamber with respect of the dangerous fraction. To provide separability, the primary and secondary chambers could be provided with a respective pair of membranes in very close proximity so that on separation virtually no material would be lost from the secondary chamber.

Normally when used with blood samples the primary chamber(s) will most commonly contain between 1 ml and 20 ml of sample. However, any container in any of the above embodiments can be reduced in volume or adapted for use with hematocrit and/or capillary blood collecting systems where the sample volume is below 1 ml.

THE DRAWINGS

To help understanding of the invention, various specific embodiments thereof will now be described by way of example and with reference to the accompanying drawings, in which:

FIGS. 1 to 18 are exploded perspective views of containers in accordance with the invention.

PREFERRED EMBODIMENTS

FIG. 1 shows the simplest embodiment of the invention. The container shown there has a single primary chamber 1 linked to a single secondary chamber 2 via a common wall 3 in which has been fused a semi-permeable membrane 4. A lid 5 for the primary chamber enables sealing of a sample (not shown) is inserted into the primary chamber 1. Once the sample has been inserted into the primary chamber and the lid closed any infectious material is hermetically sealed in as this cannot cross the semi-permeable membrane, due to the latter being provided with a cut-off matched to the molecular size of the type of sample with which the container is to be used. However, material of a lower molecular weight than the dangerous fraction can move across the membrane in either direction predominantly by dialysis or osmosis.

Although the chambers 1,2 of the container have square cross-section other geometric configurations are possible, such as, circular, rectangular or oval, possibly with tapering in any plane.

The preferred material of the chambers is clear polystyrene. They can be injection moulded and glued together and to the membrane at the common wall 3. The primary chamber 1 is open 6 at the common wall and the membrane is first glued to the region of the wall surrounding the opening. Then the membrane and the region of the wall not covered by the membrane is glued to the corresponding open side wall of the secondary chamber 2. This is carried out in a manner that while low molecular weight material is able to cross from one chamber to the other through the membrane, and no material can leak around through the sides of the membrane nor escape to the outside. As an alternative to the use of adhesive, the three components could be welded together.

In variants, the lid may be provided with sealing lips (not shown). If the primary chamber has a circular cross-section, the lid could be a screw cap, with or without a sealing gasket.

Although not limited to this material the semi-permeable membrane could be made of porous polyurephane such as Porelle 30 (TM) made by Porvair Ltd, England. This material has been shown to act as a semi-permeable membrane but which will completely restrict the movement of bacteria and viral particles. Such material can be sealed to polystyrene to form a viral tight seal.

The distance between the internal faces of the side walls 7,8 of the primary and secondary chambers can be a known dimension, such as 1 cm, and the material of the chambers can be manufactured to a specification applicable for use in a spectrophotometer or similar instrument. For example they would be made of plastics material which transmitted both visible and UV light. These same side walls can then be placed in the optical path of an inversion microscope to enable the contents of the primary chamber to be examined for the presence of pathogenic organisms. This examination would take place more easily by placing the container on its side with one of the optically clear faces placed on the microscope stage.

FIGS. 2 and 3 show an embodiment in which there is a single primary chamber 11 linked to four secondary chambers 12 via a common wall 13 in which has been fused a semi-permeable membrane 14. By having more than one secondary chambers different tests can be carried out on the same sample added to the primary chamber.

FIG. 4 shows an embodiment in which there is a multiple primary chamber 21 linked to a single secondary chamber 22 via a common wall 23 in which has been fused a semi-permeable membrane 24. By having more than one primary chambers but with a single secondary chamber the same pool of reagent can be used to perform identical or similar tests on different samples.

FIG. 5 shows an embodiment in which there is the membrane 34 which is restricted to the upper part of the chambers 31,32. In such an embodiment damage to the membrane would be minimised if the container was for example centrifuged.

By contrast, FIG. 6 shows an embodiment in which there is the membrane 44 which is restricted to the lower part of the chambers 41,42. In such an embodiment movement of material between compartments would be enhanced by for example centrifugation.

FIG. 7 shows a variant for use in semi-quantitative assays. Graduations 8 are moulded into the walls of the chamber(s) to enable the contents of the primary and secondary chambers to be defined and so allow quantitative analysis to take place. It will be appreciated that such an analysis is more easily performed if the wall of the chamber is transparent with respect of its contents.

FIG. 8 shows an embodiment in which the primary and secondary chambers 51,52 are separable. Each chamber has its own membrane 54',54" fused to the opposite common walls 53',53". The latter are lightly glued together so that after assay, the chambers can be separated, with the dangerous fraction retained in the primary chamber. As an alternative to light gluing, rupture points can be provided.

FIG. 9 shows an embodiment in which there is a single primary chamber 61 linked to two separate sets of secondary chambers 62 each of which sets has been divided into four secondary chambers 63. In this embodiment there are two semi-permeable membranes 64. By having more than one secondary chambers different tests can be carried out on the same sample. In addition by having two separate semi-permeable membranes these can have different properties which will further increase the range of tests that can be carried out. For example if one membrane had a relatively large pore size of 500,000 Daltons blood proteins could be examined in the secondary chambers distal to this membrane while for the secondary chambers on the other side a finer membrane could be present which would restrict the movement of large proteins that may interfere with certain assays.

FIG. 10 shows a variant in which the primary chamber 61',61" is sub-divided by a semi-permeable membrane 9. Sample added to only one of these chambers 61',61" sub-divides making further analysis possible. For example if the membrane 9 has a pore size of 1 micron red-blood cell free plasma or serum would be formed in the primary chamber on the opposite side of the membrane from the chamber to which the sample is added. Safe assays can then be performed in their respective secondary chambers on filtrates of whole blood or red-blood cell free serum and plasma.

FIG. 11 shows an embodiment in which there is the single primary chamber 71, linked to a series of interconnected secondary chambers 72, between each pair of which the membrane 73', 73", 73'" has a different property, whereby lighter fractions can travel furthest for appropriate assays.

Figure 14:
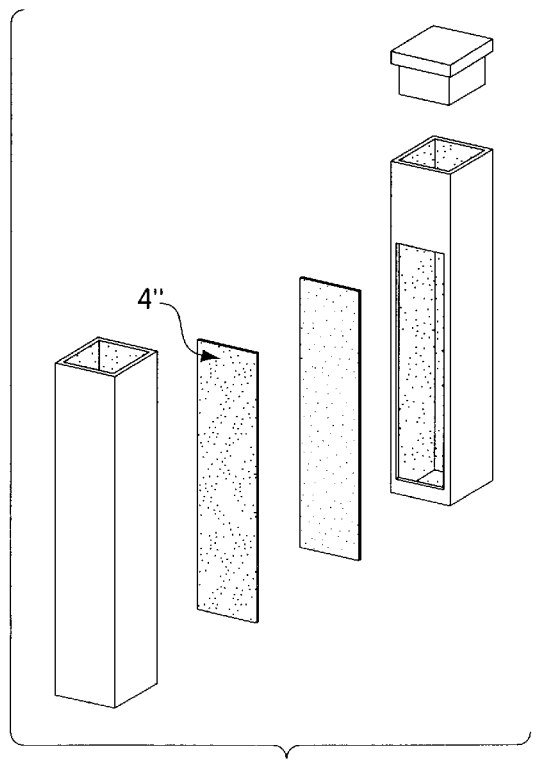

FIG. 14 a further variant in which the semi-permeable membrane is coated with a material to reduce or enhance the movement of material between the chambers. This is indicated by a separated coating layer 4" of fine dots to represent the coating. Typically this can be a chelating agent to bind heavy metals. It can be applied not only to the membrane, but also to the walls of the primary chamber.

Figure 15:
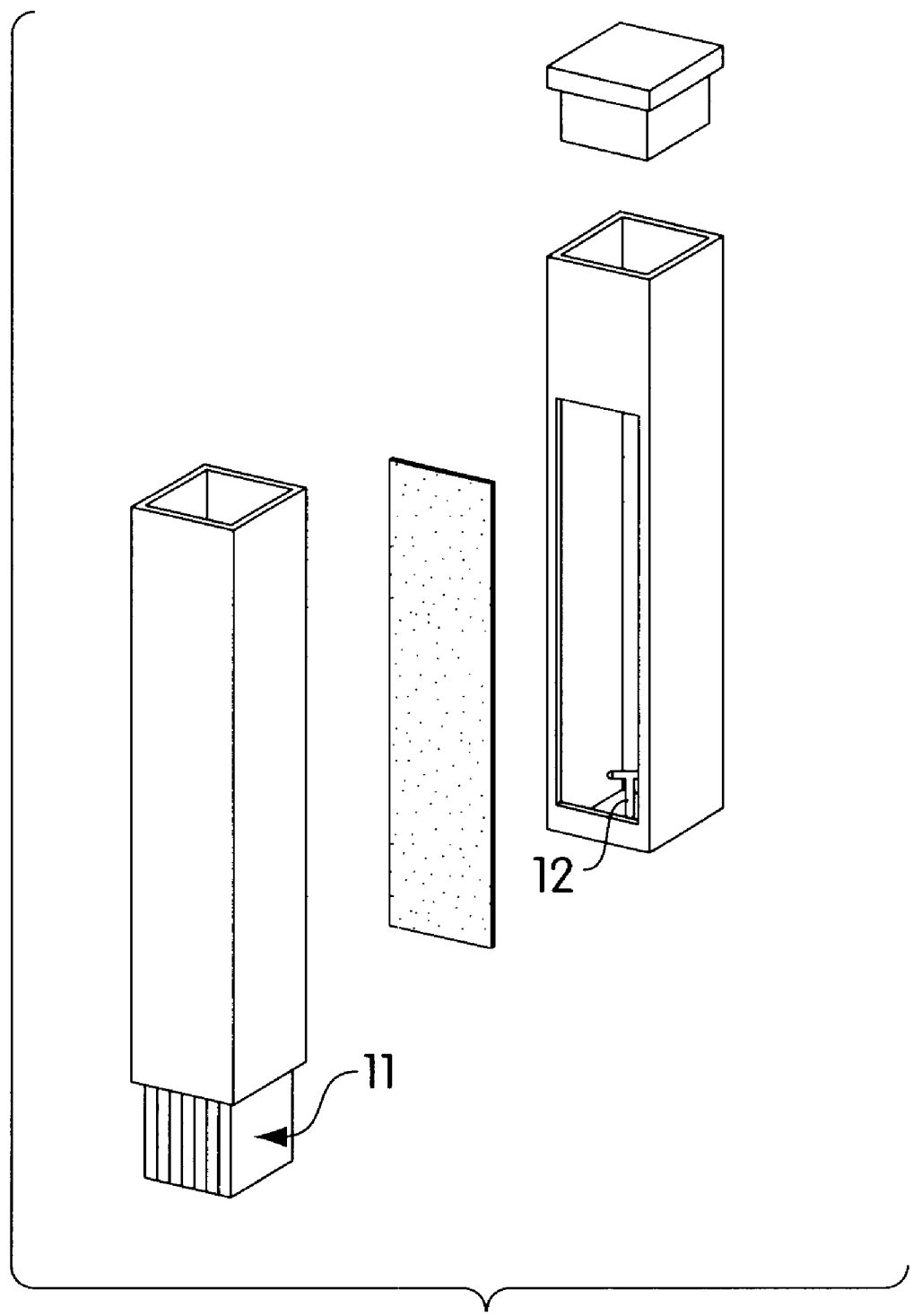

FIG. 15 shows a container having two integrally moulded components 11,12 for enhancing the agitation of the contents of the chambers. The base of the secondary chamber has been extended 11 to fit into the manifold of a proprietary laboratory agitator. Additionally, the inside of the primary chamber contains a T-shaped member 12 to agitate its contents on shaking.

Figure 12:
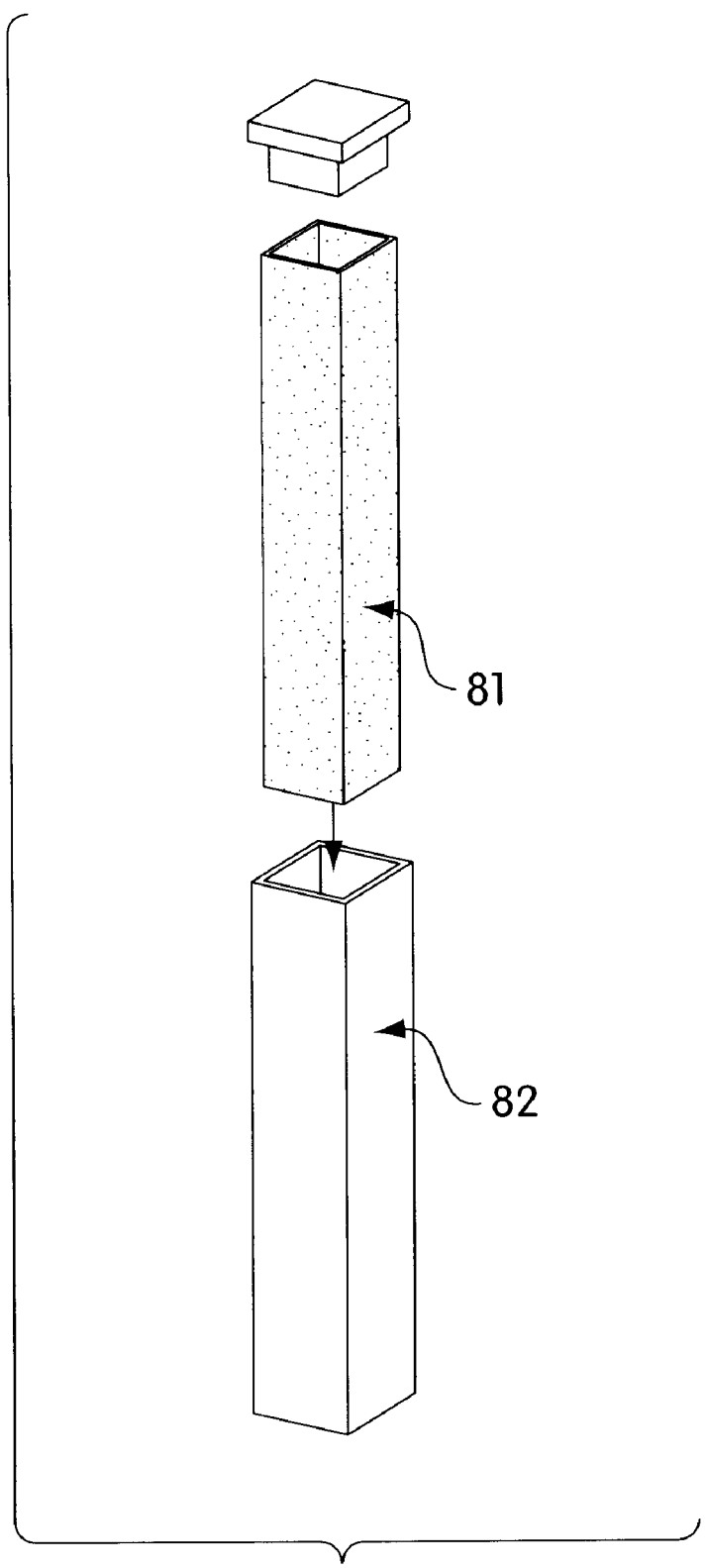
FIG. 12 shows an embodiment in which, apart from its lid, the primary chamber 81 is entirely of semi-permeable membrane and is insertable into a re-usable secondary chamber 82.
Figure 13:
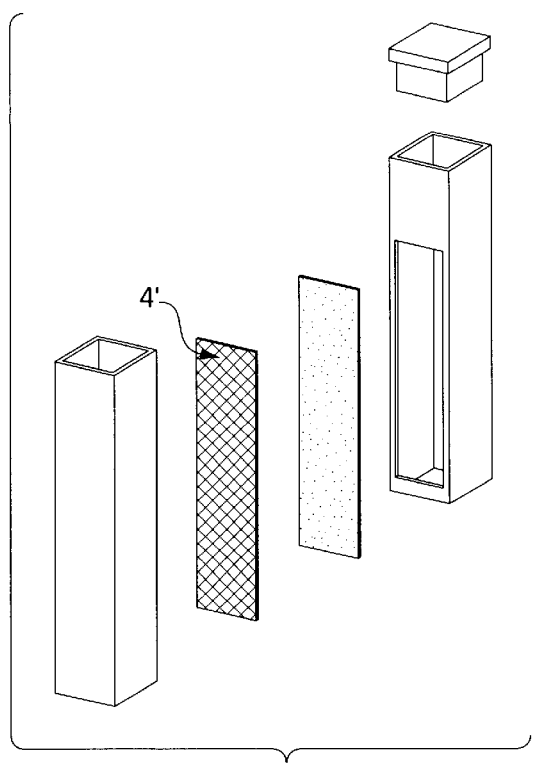
FIG. 13 shows a variant of the embodiment of FIG. 1, in which the membrane 4 is reinforced by a nylon mesh 4'.
Figure 16:
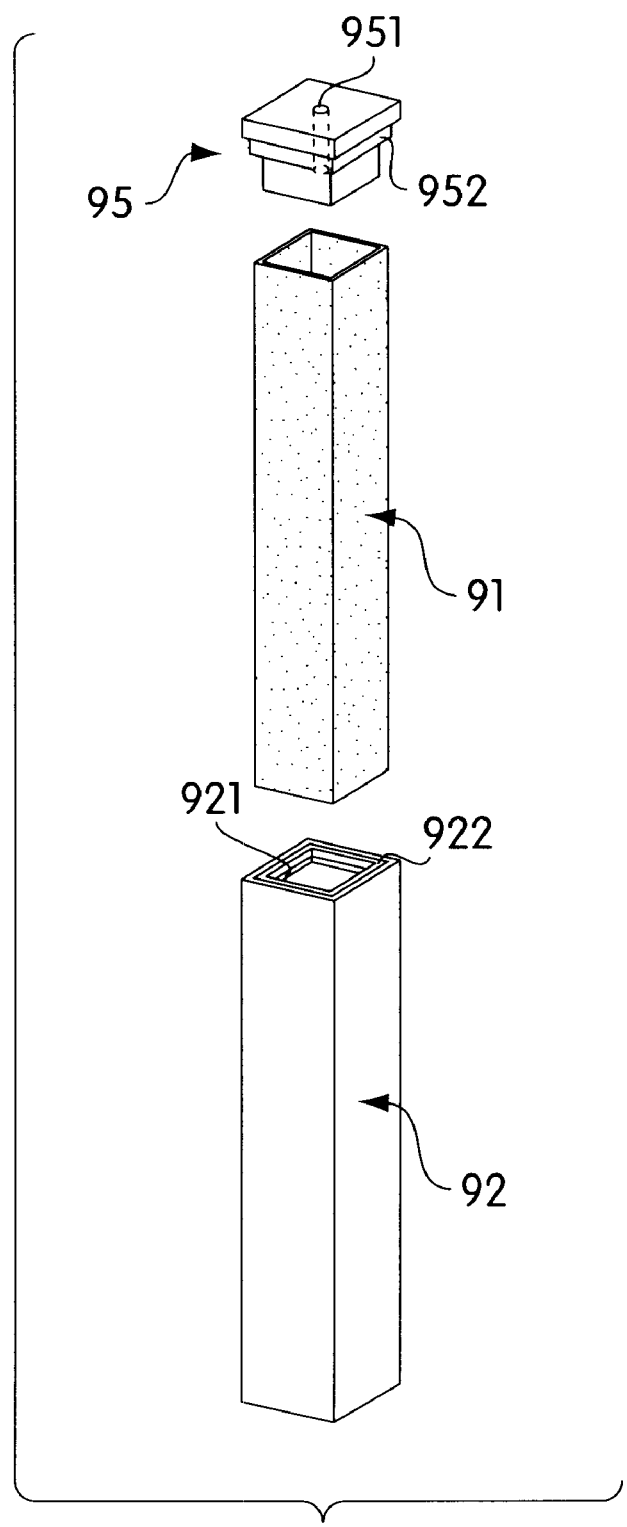

FIG. 16 shows a variant of the embodiment of FIG. 12, intended for use with a blood collection system. The primary chamber 91 is comprised of rigid or well supported semi-permeable membrane material. Into this is inserted a gas-tight lid 95 which has a pierceable, gas-tight inlet septum 951 of the type suitable to receive a hollow needle (not shown) for introduction of the sample. The secondary chamber 92 is sized to receive wholly the primary chamber. It has a flange 921 at its mouth, which supports a gas-tight seal 922 against which a flange 952 of the lid abuts. Prior to assembly appropriate solutes, solvents or solutions may be placed in any chamber. These could for example include dry anticoagulants in the primary chamber. The container is then assembled in a vacuum. On removal from the vacuum an internal vacuum is maintained within the whole container by the seal 922 and the lid 95. The result is the establishment of a vacuum in the container which draws the lid against the seal. On insertion of the needle through the port 951, which allows its passage and reseals on its withdrawal, the vacuum draws the sample into the primary chamber, and on into the secondary chamber. The amount of material that enters the secondary chamber at this time can be optimised for particular applications by adjusting the permeability of the membrane and the relative proportions of chambers 91 and 92 and the amount of sample that is added. At any time after the sample has been added to the primary chamber 91 the existing secondary chamber 92 may be separated from the primary chamber 91 at the junction of 922 and 952. This will enable reagents to be added or removed from the existing secondary chamber 92 in complete safety as the dangerous material is retained by the semi-permeable membrane. Alternatively, a further port (not shown) can be added to the secondary chamber to facilitate the removal or insertion of reagents. Alternatively the existing secondary chamber may be replaced by a different secondary chamber (not shown) that may or may not have similar proportions or function or reagents in it.

Figure 1:
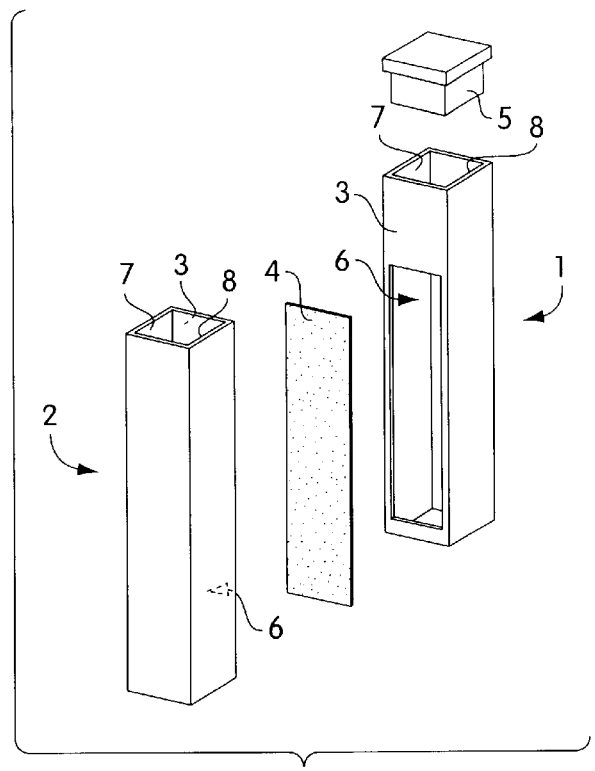
Figure 2:
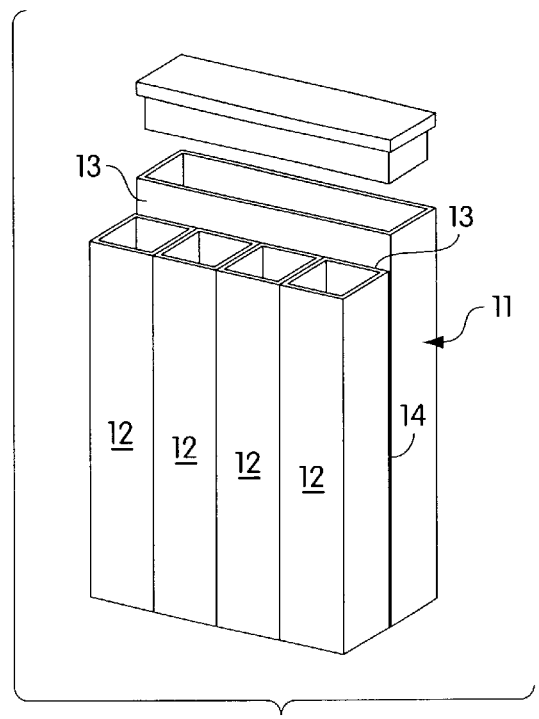
Figure 3:
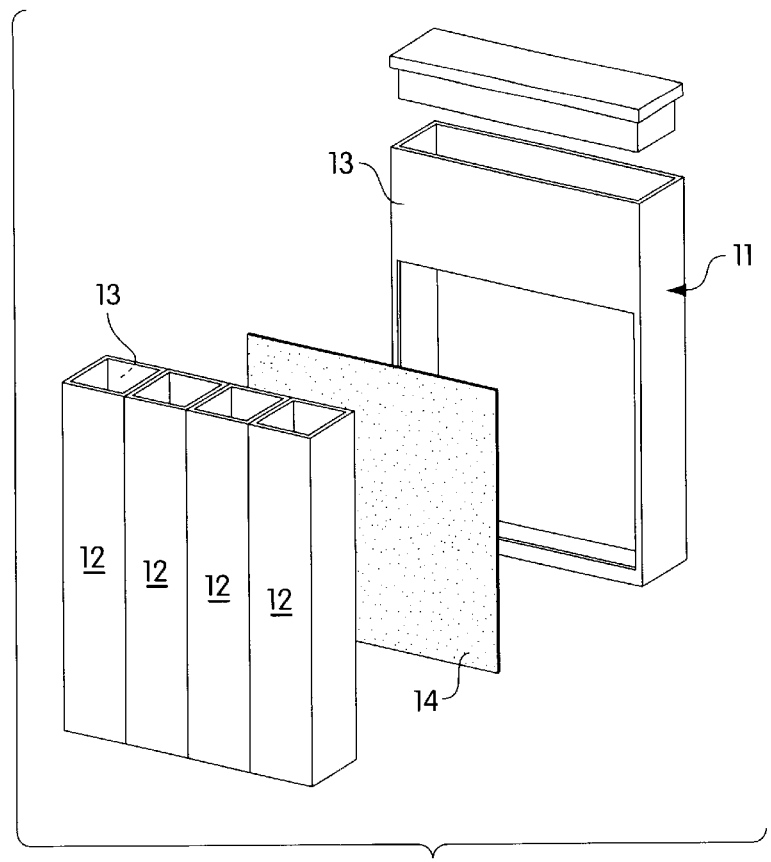
Figure 4:
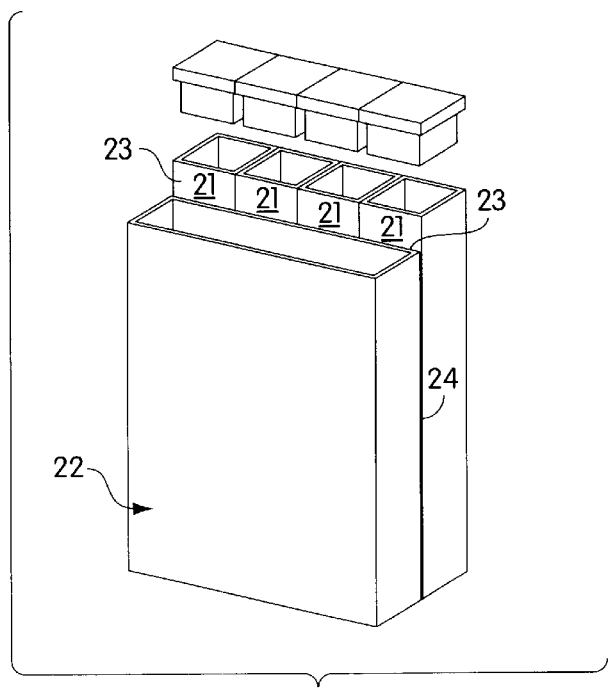
Figure 5:
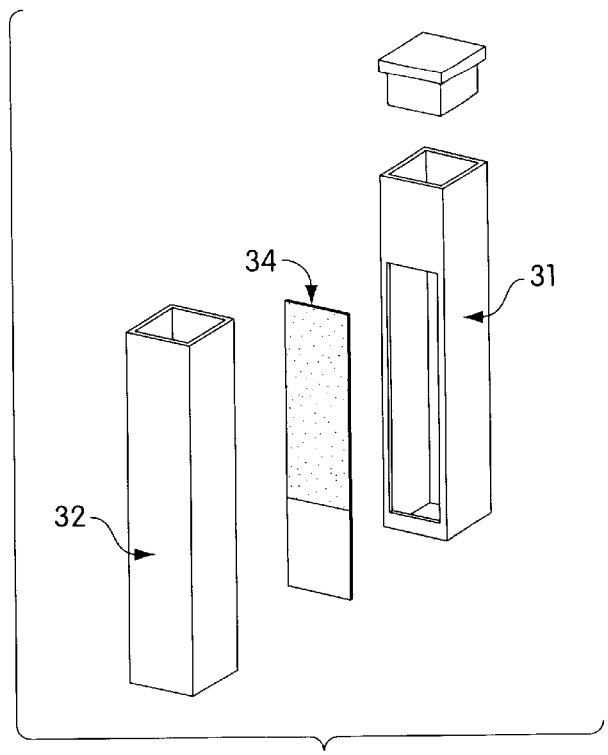
Figure 6:
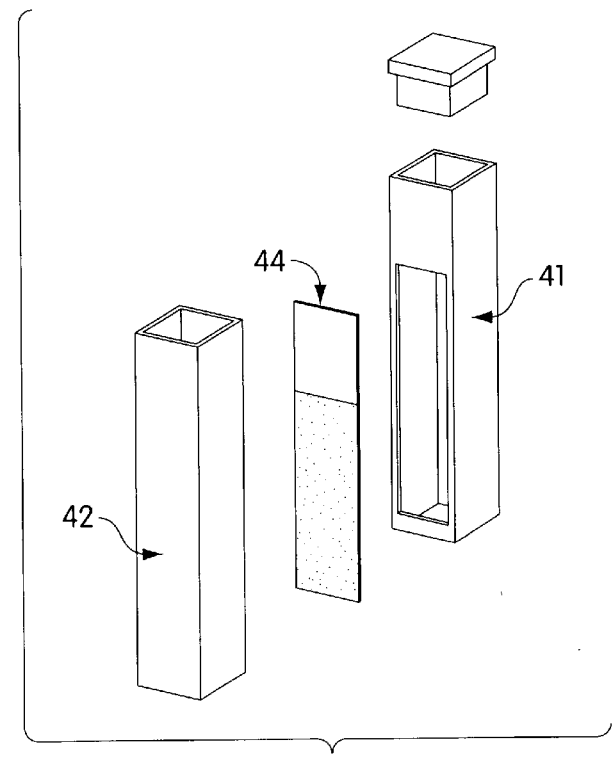
Figure 7:
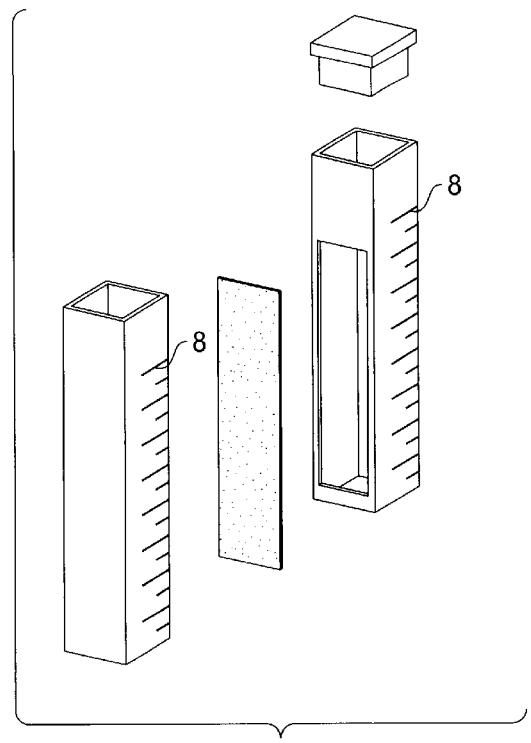
Figure 8:
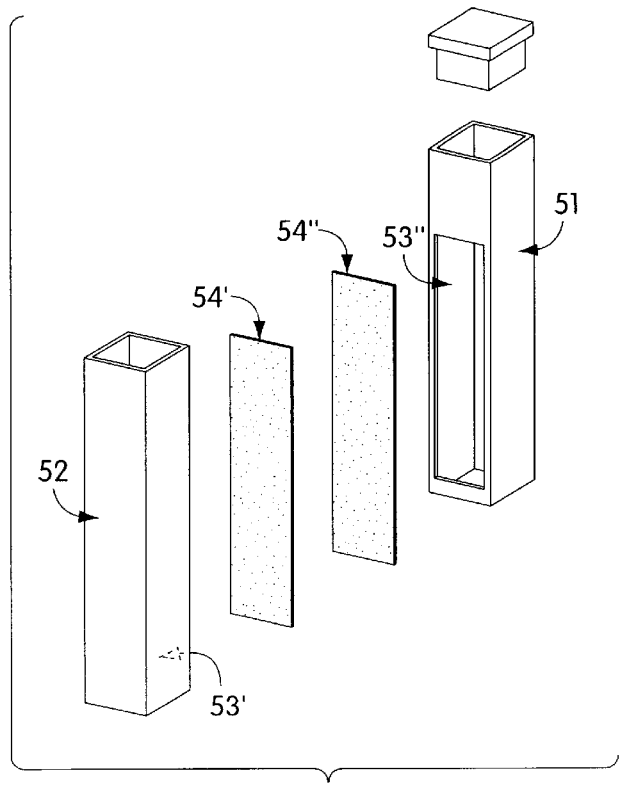
Figure 9:
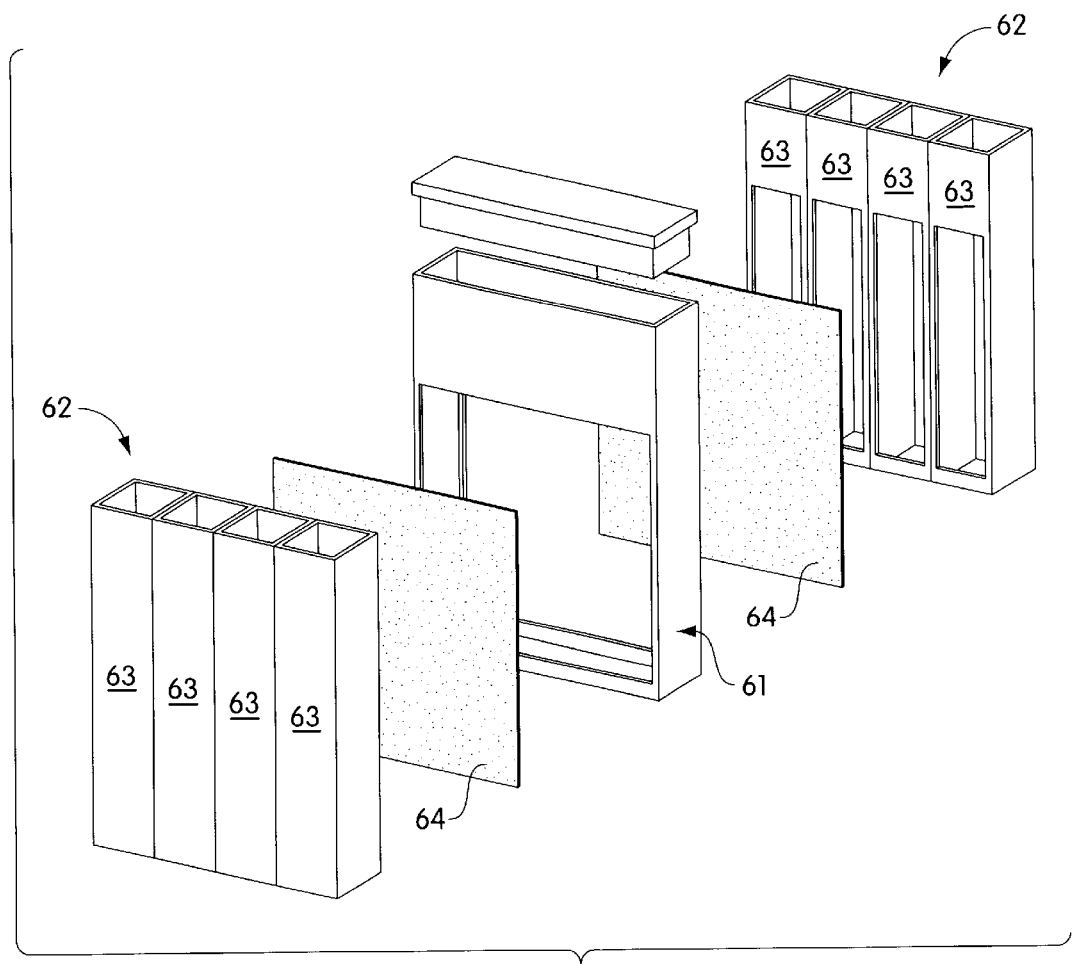
Figure 10:
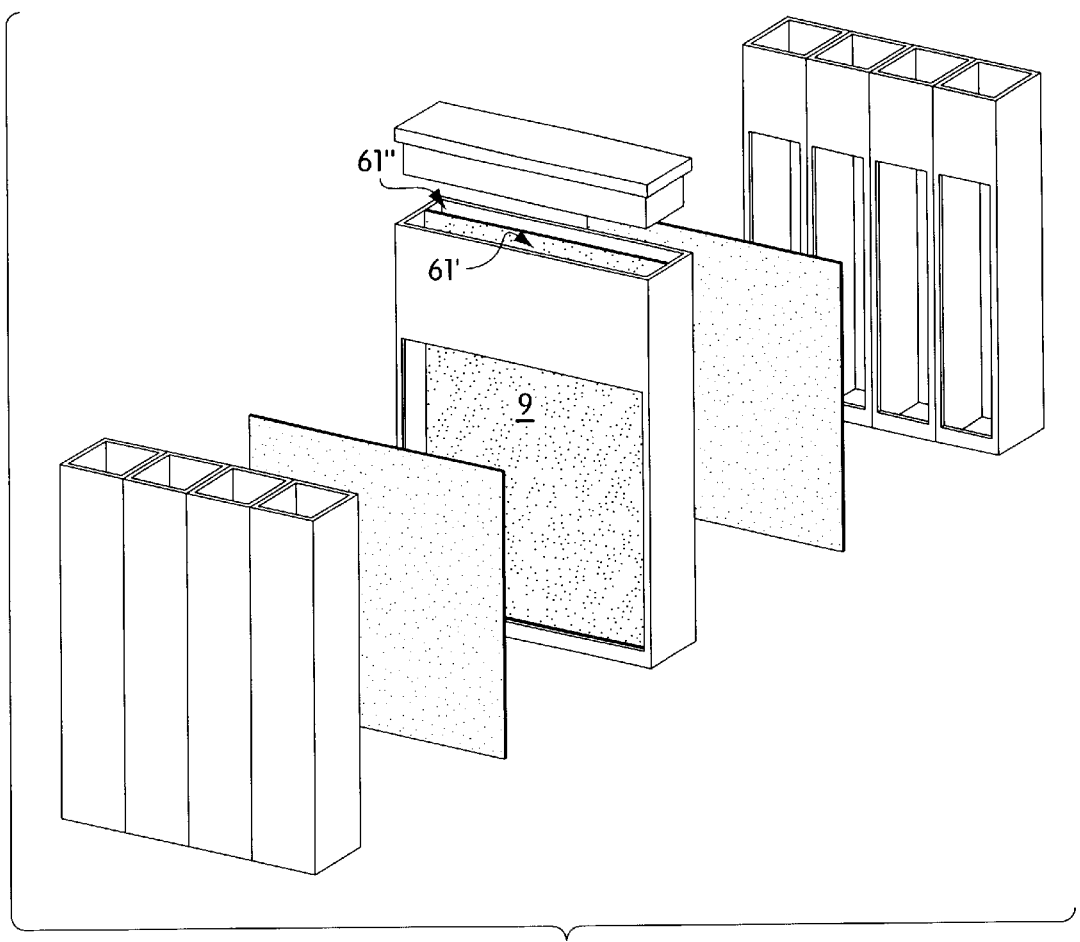
Figure 11:
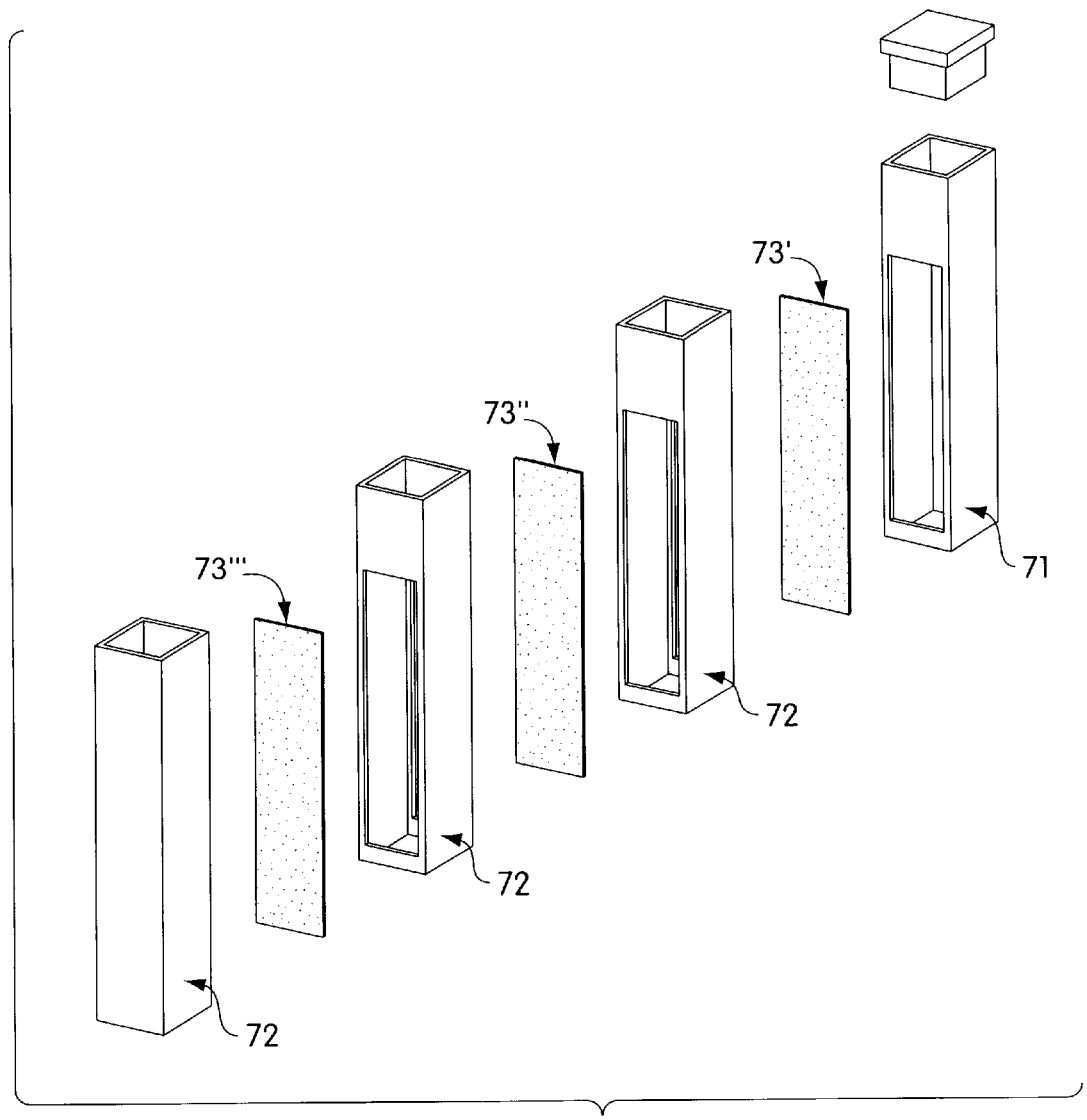
Figure 17:
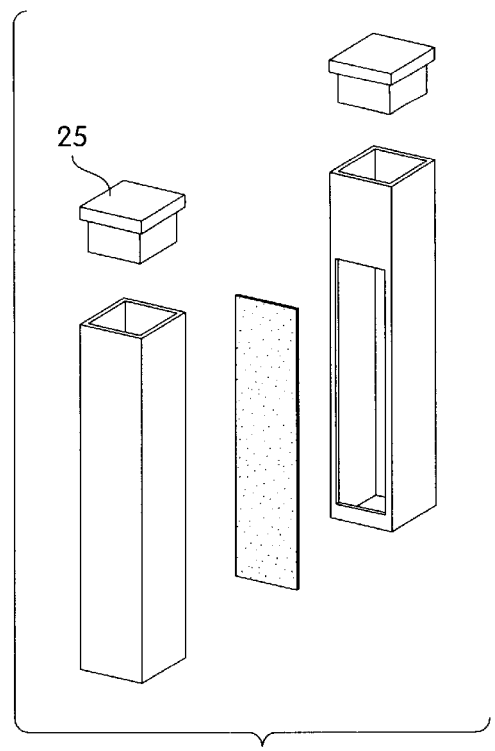

FIG. 17 is a variant of the container of FIG. 1, in which the secondary chamber is provided with a lid 25.

Figure 18:
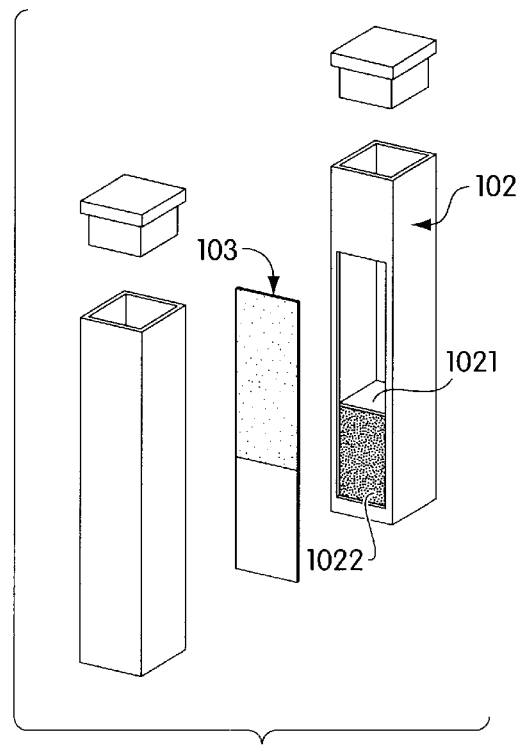

FIG. 18 shows a container with a burstable septum 1021 in the secondary chamber 102, in which can be placed labile reagents 1022. The semi-permeable membrane 103 does not extend down as far as the septum 1021, so that the contents do not immediately interact with any material in the primary chamber. At an appropriate time, the septum can be broken to release its contents, for instance by application of an object inserted through the open neck of the secondary chamber. This arrangement has particular application where a two stage reaction is employed, with the reagent(s) for the second stage being retained below the septum until the first stage has been completed.

What is claimed is:

1. A container for containing a sample liable to include a potentially infectious, toxic or dangerous material, the container comprising.

2. A container as claimed in claim 1, wherein the semi-permeable membrane occupies the upper part of the common wall.

3. A container as claimed in claim 1, wherein the semi-permeable membrane occupies the lower part of the common wall.

4. A container as claimed in claim 1, wherein the the primary chamber(s) with a dangerous fraction of the sample retained therein is/are separable from the secondary chamber(s).

5. A container as claimed in claim 4, wherein the primary chamber consists substantially of semi-permeable membrane, whereby it and its contents can be removed from the secondary chamber.

6. A container as claimed in claim 1, wherein at least one of the chambers is of clear material to allow the contents to be seen and preferably facilitate the direct assay of their contents in any part of the electromagnetic spectrum.

7. A container as claimed in claim 6, wherein there is an optically clear wall portion of one of the chambers to facilitate the direct examination of their contents using a microscope, preferably an inverted microscope via the optically clear wall portion.

8. A container as claimed in claim 1, including a single primary chamber connected to multiple secondary chambers, whereby more than one separate assays can be determined on the contents of the same primary chamber.

9. A container as claimed in claim 1, including multiple primary chambers connected to a single secondary chamber so that multiple identical or dissimilar assays can be carried out at the same time but using a common pool of reagents.

10. A container as claimed in claim 1, wherein one or more of the secondary chambers includes means for adding or removing a specific volume of mass of reagent or biological material.

11. A container as claimed in claim 1, including means for enhancing the speed and/or mass of movement of contents through the semi-permeable membrane.

12. A container as claimed in claim 1, wherein the semi-permeable membrane is coated or treated to enhance or inhibit the movement of specific solutes or solvents.

13. A container as claimed in claim 1, wherein the membrane is reinforced.

14. A container as claimed in claim 1, wherein some or all of the chambers are pre-loaded with dried or liquid reagents prior to its use.

15. A container as claimed in claim 1, wherein some or all of the chambers are pre-loaded with living or dead reference microorganisms or standard masses of reference reagents.

16. A container as claimed in claim 1, where some or all chambers contain substances which act as an osmotic driver and/or dialysing substance to enhance the movement of solvent and/or solute across the semi-permeable membrane in any appropriate direction.

17. A container as claimed in claim 1, wherein some or all chambers contain substances which are capable of rehydration and/or are hydroscopic and so enhance the movement of solvent and/or solute across the semi-permeable membrane in any appropriate direction, the substances preferably being in the secondary chamber(s) to concentrate the material in the primary chamber.

18. A container as claimed in claim 1, wherein the secondary chamber(s) is/are open to allow for the removal and/or rinsing and/or dilution of all or part of its contents.

19. A container as claimed in claim 1, wherein the secondary chamber(s) is/are provided with lid(s).

20. A container as claimed in claim 1, wherein one or more chamber contains chemical or physical binding agents that bind specific substances to reduce the movement of all or specific components that would normally move across the semi-permeable membrane and/or reduce their participation in subsequent chemical reactions.

21. A container as claimed in claim 1, wherein two or more chambers are placed in sequence each separated by a semi-permeable membrane which may have similar or dissimilar properties and structure.

22. A container as claimed in claim 1, wherein one or more of the chambers contains a device for indicating that a specific volume of liquid is present in any particular chamber to enable quantitative or at least semi-quantitative assays to be carried out.

23. A container as claimed in claim 1, wherein one or more of the chambers contain a specific substance that provides visible, chemical or physical evidence that there had been a breach of the integrity of the primary chamber(s).

24. A container as claimed in claim 1, including multiple layer membranes.

25. A container as claimed in claim 1, wherein solutes and/or solvent are retained in a sub-compartment of one or more of the chambers from which it is separated by a burstable septum which can be opened or broken at an appropriate time without affecting the total integrity of the whole chamber.

26. A container as claimed in claim 1, including substances that enhance the movement of solvents or solutes across the membrane and assay reagents incorporated into the structure or bound to the surface of the substances.

27. A method of sampling dangerous fraction, the sample being contained in one or more of the primary chamber(s) of a container as claimed in claim 1, the method including the step of:

passing material initially present in the primary chamber(s) and having a lower molecular size than the cut-off of the membraned through the membrane; and reacting the passed material with material within the secondary chamber(s) whilst the dangerous fraction is retained within the primary chamber(s).

28. A method as claimed in claim 27, including the preliminary step of culturing living organisms in the primary chamber(s).

29. A method as claimed in claim 27, in which a disinfecting substance and/or toxic neutralising agent is added to the secondary chamber(s) and allowed to permeate through the semi-permeable membrane to the primary chamber(s).

30. A method as claimed in claim 27, wherein the secondary chamber(s) contain water absorbing substances and they are allowed to extract substantially all water from the sample.

31. A method of sampling a dangerous fraction, the sample being contained in one or more of the primary chamber(s) of a container as claimed in claim 1, the method including the step of:

passing material initially present in the secondary chamber(s) and having a smaller molecular size than the cut-off of the membrane to pass through the membrane; and reacting the passed material with material within the primary chamber(s) whilst the dangerous fraction is retained within the primary chamber(s).

32. A container as claimed in claim 1, wherein at least one of the chambers is made of a clear plastics material.

33. The container of claim 1, wherein the molecular size cut-off is from 0.0001 microns to 0.7 microns.

34. The container of claim 1, wherein the molecular size cut-off is from 0.0001 microns to 0.02 microns.

35. The container of claim 1, wherein the molecular size cut-off is from 0.0001 microns to 0.006 microns.

36. The container of claim 1, wherein the molecular size cut-off is from 0.0001 microns to 0.0005 microns.

37. A container for containing a sample liable to include a potentially infectious, toxic or dangerous material, the container comprising:

one or more primary chambers for retaining potentially infectious, toxic or dangerous substances, a sealant for sealing a sample into the primary chamber(s), one or more secondary chambers linked to the primary chamber(s) via at least one common wall(s)

a vacuum seal for at least the primary chamber(s) and a seal adapted for introduction of a sample via a needle and for re-sealing after withdrawal of the needle, wherein the container can be evacuated for drawing of the sample in the container; and a semi-permeable membrane incorporated in the common wall(s), the semi-permeable membrane having a molecular weight/effective molecular diameter or configuration (i.e., molecular size) cut-off such that potentially infectious, toxic or dangerous material placed and sealed in the primary chamber(s) is retained there by virtue of having a molecular weight higher than the molecular weight cut-off of the membrane, wherein the molecular size cut-off is from 0.0001 microns to 60 microns.

38. The container of claim 37, wherein the molecular size cut-off is from 0.0001 microns to 0.7 microns.

39. The container of claim 37, wherein the molecular size cut-off is from 0.0001 microns to 0.02 microns.

40. The container of claim 37, wherein the molecular size cut-off is from 0.0001 microns to 0.006 microns.

41. The container of claim 37, wherein the molecular size cut-off is from 0.0001 microns to 0.0005 microns.

42. The container as claimed in claims 32, wherein at least one of the chambers comprises polystryene.

* * * * *

UNITED STATES PATENT AND TRADEMARK OFFICE
CERTIFICATE OF CORRECTION

PATENT NO.     : 6,506,346 B1
DATED          : January 14, 2003
INVENTOR(S)    : Philip Monro It is certified that error appears in the above-identified patent and that said Letters Patent is hereby corrected as shown below:

Column 11,
Line 36, please replace "tainer comprising," with -- tainer comprising:
    one or more primary chambers for retaining potentially infectious, toxic or dangerous substances,
    means for sealing a sample into the primary chamber(s),
one or more secondary chambers linked to the primary chamber(s) via at least one common wall(s),
    a vacuum seal for at least the primary chamber(s) and a seal adapted for introduction of a sample via a needle and for re-sealing after withdrawal of the needle, wherein the container can be evacuated for drawing of the sample in the container; and
    a semi-permeable membrane incorporated in the common wall(s),
    the semi-permeable membrane having a molecular weight/effective molecular diameter or configuration (i.e., molecular size) cut-off such that potentially infectious, toxic or dangerous material placed and sealed in the primary chamber(s) is retained there by virtue of having a molecular weight higher than the molecular weight cut-off of the membrane, wherein the molecular size cut-off from 0.0001 microns to 60 microns. --

Signed and Sealed this

Twenty-sixth Day of August, 2003

JAMES E. ROGAN
*Director of the United States Patent and Trademark Office*